United States Patent
Khoo et al.

(10) Patent No.: US 10,697,964 B2
(45) Date of Patent: Jun. 30, 2020

(54) LIQUID BIOPSY DETECTION OF LEUKEMIA USING CLOSED-LOOP MICROFLUIDICS

(71) Applicant: Massachusetts Institute of Technology, Cambridge, MA (US)

(72) Inventors: Bee Luan Khoo, Singapore (SG); Jongyoon Han, Bedford, MA (US); Kyungyong Choi, Cambridge, MA (US); Hyunryul Ryu, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 358 days.

(21) Appl. No.: 15/726,710

(22) Filed: Oct. 6, 2017

(65) Prior Publication Data
US 2018/0136210 A1    May 17, 2018

Related U.S. Application Data

(60) Provisional application No. 62/422,329, filed on Nov. 15, 2016.

(51) Int. Cl.
*G01N 33/574* (2006.01)
*B01L 3/00* (2006.01)
(Continued)

(52) U.S. Cl.
CPC ........ *G01N 33/574* (2013.01); *B01L 3/50273* (2013.01); *B01L 3/502715* (2013.01);
(Continued)

(58) Field of Classification Search
CPC .................. G01N 33/574; B01L 3/502715
See application file for complete search history.

(56) References Cited

U.S. PATENT DOCUMENTS 9,789,485 B2   10/2017   Han et al.
2008/0128331 A1   6/2008   Lean et al.
(Continued)

FOREIGN PATENT DOCUMENTS

WO    2011109762 A1   9/2011
WO    2013181615 A1   12/2013
(Continued)

OTHER PUBLICATIONS

Clinical Validation of an Ultra High-Throughput Spiral Microfluidics for the Detection and Enrichment of Viable Circulating Tumor Cells. Khoo et al. PLOS One Jul. 2014, vol. 9, Issue 7 (Year: 2014).*
(Continued)

*Primary Examiner* — Krishnan S Menon
*Assistant Examiner* — Dwan A Gerido
(74) *Attorney, Agent, or Firm* — Elmore Patent Law Group, P.C.; Carolyn Elmore; Mahreen Hoda

(57) ABSTRACT

This invention describes a one-step technique for the simultaneous label-free detection and concentration of blast cells from a blood sample. Enrichment of blast cells is achieved using a closed loop microfluidics system, allowing continuous removal of waste and non-target cells to generate concentrated samples of high purity without the need for specific targeting of proteins by antibodies. The technique is highly effective for samples which cannot be purified in a single run. The application of detecting rare blast cells for monitoring minimal residual disease in leukemia patients is demonstrated. The sensitivity of the invention promotes the detection of blast cells in blood samples of early-stage patients.

27 Claims, 8 Drawing Sheets

(51) Int. Cl.
*G01N 33/50* (2006.01)
*G01N 33/569* (2006.01)

(52) U.S. Cl.
CPC .... *B01L 3/502761* (2013.01); *G01N 33/5073* (2013.01); *G01N 33/56966* (2013.01); *G01N 33/57488* (2013.01); *B01L 2300/0627* (2013.01); *B01L 2300/088* (2013.01); *B01L 2300/0864* (2013.01); *B01L 2300/0883* (2013.01); *B01L 2400/0409* (2013.01)

(56) References Cited

U.S. PATENT DOCUMENTS

| | | |
|---|---|---|
| 2011/0070581 A1 | 3/2011 | Gupta et al. |
| 2011/0189150 A1 | 8/2011 | Bosch et al. |
| 2014/0093867 A1* | 4/2014 | Burke ............... G01N 1/4077 435/5 |
| 2014/0248621 A1* | 9/2014 | Collins ............. G01N 15/1031 435/6.12 |
| 2015/0238963 A1* | 8/2015 | Han .................. B01L 3/502753 435/30 |
| 2015/0293010 A1 | 10/2015 | Nagrath et al. |
| 2016/0032350 A1 | 2/2016 | Hou et al. |
| 2016/0199853 A1 | 7/2016 | Harwood et al. |
| 2016/0303565 A1* | 10/2016 | Bhagat .............. G01N 15/0255 |
| 2017/0292104 A1* | 10/2017 | Ebrahimi Warkiani ..................... C12M 23/02 |
| 2018/0128723 A1 | 5/2018 | Ryu et al. |

FOREIGN PATENT DOCUMENTS

| | | |
|---|---|---|
| WO | 2014046621 A1 | 3/2014 |
| WO | 2014152643 A2 | 9/2014 |
| WO | 2015156876 A2 | 10/2015 |
| WO | 2016/044537 A1 | 3/2016 |
| WO | 2016044537 A1 | 3/2016 |
| WO | 2016044555 A1 | 3/2016 |
| WO | 2016077055 A1 | 5/2016 |

OTHER PUBLICATIONS

An ultra-high-throughput spiral microfluidic biochip for the enrichment of circulating tumor cells. Warkiani et al. Analyst, 2014, 139, 3245 (Year: 2014).*
Inertial microfluidics for continuous particle separation in spiral microchannels. Sathyakumar S. Kuntaegowdanahalli, Ali Asgar S. Bhagat, Girish Kumar, Ian Papautsky Lab Chip, 2009, 9, 2973-2980 (Year: 2009).*
Hou, H.W., et al., "Isolation and Retrieval of Circulating Tumor Cells Using Centrifugal Forces," Scientific Reports, vol. 3(1259): pp. 1-8 (Feb. 2013).
Nan, L., et al., "Emerging Microfluidic Devices for Cell Lysis: a Review," Lab on a Chip, vol. 14, pp. 1060-1073 (2014).
Gansler, T., et al., "Sixty Years of CA: A Cancer Journal for Clinicians," CA Cancer J. Clin., 60(6): pp. 345-350 (2010).
Mantovani, A., "Inflaming Metastasis," Nature 457(7225): pp. 36-37 (2009).
Khoo, B.L., et al., Genesis of Circulating Tumor Cells Through Epithelial-Mesenchymal Transition as a Mechanism for Distant Dissemination in Circulating Tumor Cells, Springer (2016).
Basik, M., et al., "Biopses: Next-Generation Biospecimens for Tailoring Therapy," Nat. Rev. Clin. Oncology, vol. 10, pp. 437-450 (2013).
De Bono, J.S., et al., "Circulating Tumor Cells Predict Survival Benefit from Treatment in Metastatic Castration-Resistant Prostate Cancer," Clin. Cancer Res., 14(19): pp. 6302-6309 (2008).
Khoo, B.L., et al., "Short-Term Expansion of Breast Circulating Cancer Cells Predicts Response to Anti-Cancer Therapy," Oncotarget, 2015.
Nole, F., et al., "Variation of Circulating Tumor Cell Levels During Treatment of Metastatic Breast Cancer: Prognostic and Therapeutic Implications," Ann Oncol., 19(5): pp. 891-897 (2008).
Frisch, B., et al., "Bone Marrow Histology in Myelodysplastic Syndrome," Scand J. Haematol Supp., 45: pp. 21-37 (1986).
Whitesides, G.M., "The Origins and the Future of Microfludics," Nature 442(7101): pp. 368-373 (2005).
Bastos-Oreiro, M., et al., "Prognostic Impact of Minimal Residual Disease Analysis by Flow Cytometry in Patients with Acute Myeloid Leukemia Before and After Allogeneic Hemopoietic Stem Cell Transplantation," Eur. J. Haematol, 93(3): pp. 239-246 (2014).
Warkiani, M.E., et al., "Ultra-Fast Label-Free Isolation of Circulating Tumor Cells from Blood Using Spiral Microfluidics," Nat. Protoc., 11(1): pp. 134-148 (2016).
Warkiani, M.E., et al., "Slanted Spiral Microfludics for the Ultra-Fast, Label-Free Isolation of Circulating Tumor Cells," Lab on a Chip 14(1): pp. 128-137 (2014).
Warkiani, M.E., et al., "Malaria Detection Using Inertial Microfluidics," Lab Chip 15(4): pp. 1101-1109 (2015).
Nima, Z.A., et al., "Circulating Tumor Cell Identification by Functionalized Silver-Gold Nanorods with Multicolor, Super-Enhanced SERS and Photothermal Resonances," Sci Rep., vol. 4, p. 4752 (2014).
Nagrath, S., et al., "Isolation of Rare Circulating Tumour Cells in Cancer Patients by Microchip Technology," Nature 450(7173): pp. 1235-1239 (2007).
Jing, T., et al., Jetting Microfluidics with Size-Sorting Capability for Single-Cell Protease Detection, Biosens Bioelectron, vol. 66, pp. 19-23 (2015).
Buccisano, F., et al., "Prognostic and Therapeutic Implications of Minimal Residual Disease Detection in Acute Myeloid Leukemia," Blood 119(2): pp. 332-341 (2012).
Amin, H.M., et al., "Having a Higher Blast Percentage in Circulation Than Bone Marrow: Clinical Implications in Myelodysplastic Syndrome and Acute Lymphoid and Myeloid Leukemias," Leukemia 19(9): pp. 1567-1572 (2005).
U.S. Appl. No. 15/726,746, filed Oct. 6, 2017, titled "Particle Isolation/Enrichment Using Continuous Closed-Loop Spiral Microfludics," Ryu, et al.

* cited by examiner

LIQUID BIOPSY DETECTION OF LEUKEMIA USING CLOSED-LOOP MICROFLUIDICS

RELATED APPLICATION

This application claims the benefit of U.S. Provisional Application No. 62/422,329 filed Nov. 15, 2016. The entire teachings of the above-referenced application are incorporated herein by reference.

BACKGROUND OF THE INVENTION

Globally, cancer is one of humanity's most pressing conditions, with over 14.1 million new cases and 8.2 million deaths each year [1]. Tumor metastasis occurs when tumors shed cancer cells into the bloodstream and lymphatic system [2]. The tumor cells persisting in the peripheral blood stream are termed as circulating tumor cells (CTCs) [3] and can be detected by liquid biopsy (blood withdrawal) [4]. CTC counts demonstrate correlation with patient survival [5, 6] and cancer progression [7].

In the management of biological diseases, early detection and intervention is the key to promote therapeutic success. For leukemia, the golden standard is bone marrow biopsy [8], which is undesirable for several reasons; there are issues associated with high costs, the complexity of surgical procedure, the discomfort of such an invasive procedure as well as an increased risk of mortality. Due to these factors, monitoring mutations or blast cell levels from bone marrow biopsies is a tedious process as these procedures have to be carried out on a routine basis. In cases where these procedures cannot be done (e.g. patient is too weak for surgery), the lack of conclusive screens may affect the evaluation of disease and treatment outcome. Clinicians are keen to introduce rapid and efficient screens for leukemia by employing the use of microfluidic-based assays, which is operated with minimal reagents and samples [9].

In patients with acute myeloid leukemia (AML) and other leukemia types, leukemia spreads when immature white blood cells, termed as blast cells, are released from the bone marrow into the circulation. Blast cell counts from bone marrow can be isolated by flow cytometry [10], and the counts act as a diagnostic marker for leukemia. However, the technical limitations of flow cytometry prevent the isolation of blast cells from blood of patients with low blast cell counts (e.g. those with minimal residual disease (MRD). More specific detection methods (MRD<$10^{-5}$), such as allele-specific oligonucleotide polymerase chain reaction (ASO-PCR) and deep sequencing could be used on bone marrow samples, but these techniques involve a high level of technical complexity and are not applicable to most patients [11]. A "liquid biopsy" approach capitalizing on blood-derived blast cells for leukemia would be a low-cost, less invasive alternative to bone marrow biopsy. The sensitive detection of residual blood-derived blast cells will provide clinicians with therapeutic guidelines and bring tremendous benefits in the monitoring of patient prognosis [12].

At present, there are no procedures to enrich blast cells from blood. Comparisons of more sensitive detection methods, such as deep sequencing, has been used to demonstrate the ineffectiveness of flow cytometry on detecting bone marrow blast cells. If applied to blood-derived blast cells, flow cytometry will lead to false negatives as the proportion of blast cells in blood is relatively lower than that in bone marrow, and diluted amongst other blood cell populations (>5%). Patients with minimal residual disease (MRD) have 1 cancer cell in 10,000 or 100,000 leukocytes, while those with chronic stages of leukemia present even lower levels of blast cells (<5%). Low residual disease levels (MRD<10-5) are often not detectable by existing diagnostic procedures.

We previously demonstrated the use of inertial-based microfluidics for sorting circulating tumor cells from peripheral blood of patients with solid tumors [13, 14]. We also demonstrated the enrichment of infected malaria blood cells with relevance in disease detection using inertial-based microfluidics [15]. In contrast to other cell sorting microfluidics [16-18], inertial-based microfluidics allows high processing rates. Cell sorting microfluidics are hindered by two common limitations: 1) generating large output volumes due to the need of high dilution factors and; 2) slow processing speed due to compact cellular interactions which leads to biofouling (clogging) of the device. Subsequent steps to concentrate outputs lead to high degrees of target cell losses, further compromising the sensitivity of target cell detection.

Conventional macroscale methods for separation of cells include physical filtration using a membrane-based filter and density gradient centrifugation which exploit differences in cell size, deformability, and density to filter out target cells. These techniques are labor-intensive and require multi-step sample preparations which may introduce artifacts or lead to loss of desired cells. Membrane filtration methods are also easily susceptible to clogging and require frequent cleaning. Further, evidence of mechanical stress-induced changes in original phenotype of target cells subjected to filtration and centrifugation techniques has also been reported. Recently, inertial microfluidic devices were explored as a filter-less size-based cell fractionation method [19][20].

However, there is a continuing need to develop simpler and more efficient techniques to process blood samples that can minimize cell loss and maintain the original target cell phenotype for subsequent analysis.

SUMMARY OF THE INVENTION

The invention is generally directed to a one-step detection of leukemia using blood processed with a continuous closed-loop microfluidics device. In specific aspects, the invention is directed to a method of detecting blast cells in a blood sample comprising the step of processing blood in a continuous closed-loop micro-fluidic device. In yet another aspect, the invention is directed to a method of separating blast cells from a sample comprising the step of processing blood in a continuous closed-loop micro-fluidic device. A preferred microfluidic system comprises: (a) At least one inlet reservoir; (b) At least one output reservoir; and (c) A first curvilinear microchannel comprising a first inlet in fluid communication with an inlet reservoir, a first outlet in fluid connection with the inlet reservoir, and a second outlet in fluid communication with an output reservoir; wherein said curvilinear microchannel is configured to separate particles from a mixture of particles; and wherein the microfluidic system is configured to provide a closed-loop recirculation of separated particles (or the fluid comprising the separated particles and/or the fluid in the inlet reservoir and/or the fluid comprising the blast cells) through the first curvilinear microchannel. In certain aspects, the first curvilinear microchannel is configured to separate blast cells from a blood sample.

Preferred microfluidic devices have curved micro-channels for particle focusing and mixing.

In a particular aspect, the invention is directed to a method comprising processing blood in a microfluidic device that includes at least one inlet and a curvilinear microchannel having a trapezoidal cross section defined by a radially inner side, a radially outer side, a bottom side, and a top side, the cross section having a) the radially inner side and the radially outer side unequal in height, or b) the radially inner side equal in height to the radially outer side, and wherein the top side has at least two continuous straight sections, each unequal in width to the bottom side. The microfluidic device includes at least one outlet. In certain aspects, the microfluidic device includes at least two outlets. In yet additional aspects, the microfluidic device includes at least three outlets. In certain aspects, the microfluidic device includes two outlets. In yet additional aspects, the microfluidic device includes three outlets. In some aspects, the microfluidic device includes a single inlet. In certain aspects, the microfluidic device includes a third outlet in fluid communication with a second output reservoir or in fluid communication with the same output reservoir as the second outlet.

In some aspects, the cross section of the microfluidic device can have (a) the height of the radially inner side larger than the height of the radially outer side, or (b) the height of the radially inner side smaller than the height of the radially outer side, or (c) the top side including at least one step forming a stepped profile, or (d) the top side including at least one shallow region in between the radially inner side and the radially outer side. The trapezoidal cross section can be a right trapezoidal cross section. In certain aspects, the top and/or bottom sides of the trapezoidal cross section can be curved, with a curvature that can be convex or concave.

In other aspects, the radially inner side and the radially outer side of the trapezoidal cross section can have a height in a range of between about 20 microns (µm) and about 200 µm. In certain aspects, the top side and the bottom side of the trapezoidal cross section can have a width in a range of between about 100 µm and about 2000 µm.

In one aspect, the curvilinear microchannel can be a spiral microchannel. In another aspect, the curvilinear microchannel can be a serpentine microchannel. The curvilinear microchannel can have a radius of curvature in a range of between about 2.5 mm and about 25 mm, and a length in a range of between about 4 cm and about 100 cm.

The methods comprise introducing the sample into at least one inlet of a microfluidic device as described herein at a flow rate that isolates the blast cells. The method can include collecting by size the cells from the first outlet. In one aspect, the flow rate can be in a range of between about 0.5 mL/min and about 10 mL/min.

In additional aspects, the invention is directed to a method of detecting blast cells in a blood sample comprising the steps of:
a. introducing a blood sample into an inlet reservoir of a microfluidic system comprising:
  i. At least one inlet reservoir;
  ii. At least one output reservoir;
  iii. A first curvilinear microchannel comprising a first inlet in fluid communication with an inlet reservoir, a first outlet in fluid connection with the inlet reservoir, and a second outlet in fluid communication with an output reservoir; wherein said curvilinear microchannel is configured to separate particles from a fluid comprising a mixture of particles and wherein the microfluidic system is configured to provide a closed-loop recirculation of the fluid through the first curvilinear microchannel;
b. directing the blood sample from the inlet reservoir into the first inlet of the first curvilinear microchannel, bifurcating the fluid into a first stream containing blast cells and at least one additional stream, wherein the at least one additional stream contains waste;
c. directing the first stream to the inlet reservoir and the second stream to the output reservoir, wherein the first stream comprises blast cells; and
d. detecting blast cells in the first stream.

In additional aspects, the first curvilinear microchannel comprises a third outlet, optionally in fluid communication with the output reservoir (the same output reservoir as the second outlet) or with a second output reservoir. In yet additional aspects, the curvilinear microchannel has a trapezoidal cross section defined by a radially inner side, a radially outer side, a bottom side, and a top side, the cross section having a) the radially inner side and the radially outer side unequal in height, or b) the radially inner side equal in height to the radially outer side, and wherein the top side has at least two continuous straight sections, each unequal in width to the bottom side;
  wherein the second outlet is located on the radially inner side of the microchannel,
  wherein the third outlet is located on the radially outer side or the microchannel, and
  wherein the first outlet is located on the microchannel between the second and third outlets.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale emphasis instead being placed upon illustrating embodiments of the present invention.

DETAILED DESCRIPTION OF THE INVENTION

Figure 1:
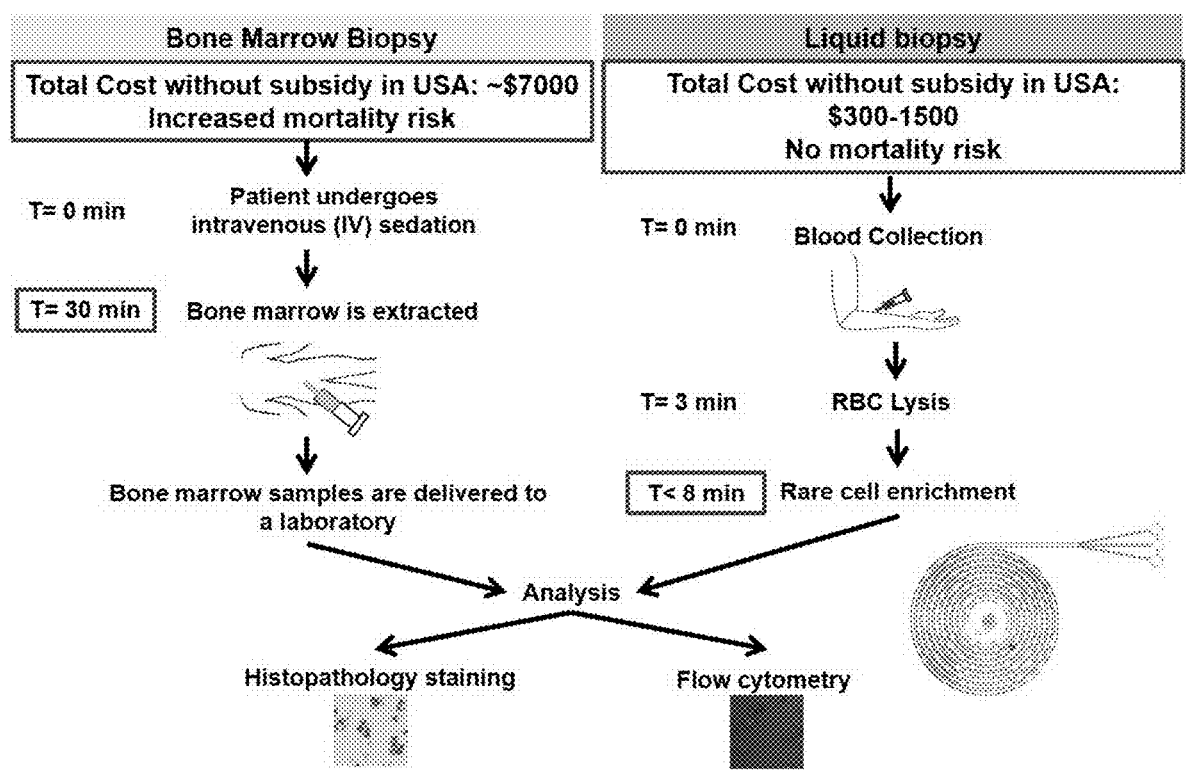
FIG. 1: Schematic overview depicting the procedure for routine leukemia evaluation detection via conventional bone marrow biopsy and liquid biopsy methods. In the case of the conventional method, blast cells are extracted from bone marrow via an invasive and painful surgical procedure. Cells may be identified by histopathological analysis or flow cytometry. In addition, bone marrow biopsies are costly procedures and may increase mortality risks. Detection threshold limits also affect effective identification of disease in patients with low blast cell counts. Conversely, blast cells can be isolated rapidly (1.5 ml/min) from liquid biopsies using a closed loop microfluidics assay. In this procedure, a small volume of blood is obtained from patients for blast cell enrichment with microfluidics. A liquid biopsy is a relatively non-invasive procedure and is cost-effective, promoting routine evaluation for disease monitoring.

A description of preferred embodiments of the invention follows.

As used herein, the words "a" and "an" are meant to include one or more unless otherwise specified. For example, the term "a cell" encompasses both a single cell and a combination of two or more cells.

The term "particle" or "particles" includes cells.

A "patient" is an animal to be treated or diagnosed or in need of treatment or diagnosis, and/or from whom a biofluid is obtained. The term "patient" includes a human.

The present invention includes a micro-fluidic system and methods of use thereof, wherein the micro-fluidic system has a closed-loop configuration in which inertial microfluidic separation of particles and/or cells is continuously repeated by feeding part of the output back to the input so that the purity and/or concentration of blast cells is maximized. The present invention includes methods for separating blast cells from a blood sample and/or methods for detecting blast cells from a blood sample comprising the steps of:
 a. introducing a blood sample into an inlet reservoir of a microfluidic system comprising:
  i. At least one inlet reservoir;
  ii. At least one output reservoir;
  iii. A first curvilinear microchannel comprising a first inlet in fluid communication with an inlet reservoir, a first outlet in fluid connection with the inlet reservoir, and a second outlet in fluid communication with an output reservoir; wherein said curvilinear microchannel is configured to separate particles from a fluid comprising a mixture of particles and wherein the microfluidic system is configured to provide a closed-loop recirculation of the fluid through the first curvilinear microchannel;
 b. directing the blood sample from the inlet reservoir into the first inlet of the first curvilinear microchannel, bifurcating the blood sample into a first stream containing blast cells and at least one additional stream, wherein the at least one additional stream contains waste;
 c. directing the first stream to the inlet reservoir and the second stream to the output reservoir, wherein the first stream comprises blast cells.

The micro-fluidic systems can comprise a curvilinear microchannel. The curvilinear microchannel can, for example, be spiral or serpentine. In certain aspects, the curvilinear microchannel is a spiral microchannel. As explained in more detail herein, blast cells can be collected from the inlet reservoir. The term "inlet reservoir" is used in the context of the reservoir from which fluid is introduced into the first inlet of the first curvilinear microchannel. The term "output reservoir" is used in the context of a reservoir into which fluid from at least one outlet of the first curvilinear microchannel is directed. In certain cases, the output reservoir can be used to collect waste.

The micro-fluidic system can be configured to separate blast cells from a blood sample. The micro-fluidic system can be configured to separate particles from a sample fluid and/or to separate blast cells from a blood sample, for example, by comprising a curvilinear microchannel with non-rectangular cross-sections. Micro-fluidic systems with non-rectangular cross-sections are described, for example, in WO2014/046621, the contents of which are incorporated by reference herein. By designing appropriate channel parameters, small particles/cells are trapped in the vortex at the outside of the microchannel wall (the outer wall) and larger particles focus along the inner microchannel wall. An example of a non-rectangular cross-section is a trapezoidal cross-section. For example, the curvilinear microchannel has a trapezoidal cross section defined by a radially inner side, a radially outer side, a bottom side, and a top side, the cross section having a) the radially inner side and the radially outer side unequal in height, or b) the radially inner side equal in height to the radially outer side, and wherein the top side has at least two continuous straight sections, each unequal in width to the bottom side. In certain aspects, the cross-section of the curvilinear microchannel has (a) the height of the radially inner side larger than the height of the radially outer side, or (b) the height of the radially inner side is smaller than the height of the radially outer side, or (c) the top side includes at least one step forming a stepped profile, or (d) the top side includes at least one shallow region in between the radially inner side and the radially outer side. In further aspect, the trapezoidal cross-section is a right trapezoidal cross section.

In certain embodiments, the curvilinear microchannel is a spiral microchannel that has a trapezoidal cross-section and wherein the curvilinear microchannel comprises three outlets. For example, the second outlet can be located on the radially inner side of the microchannel, the third outlet can be located on the radially outer side or the microchannel, and the first outlet can be located on the microchannel between the second and third outlets, wherein the stream comprising blast cells is directed to the first outlet and into the inlet reservoir.

As described herein, the methods and microfluidic system provide for recirculation of the sample through the curvilinear microchannel, in some cases, a spiral microchannel. The sample is cycled or passed through the curvilinear microchannel more than once. For example, the sample fluid (or the fluid in the inlet reservoir) can be passed through the curvilinear microchannel at least twice, at least three times, at least four times, at least five times, at least six times, at least seven times, at least eight times, at least nine times, at least ten times, or at least twenty times. The sample fluid (or the fluid introduced to the inlet reservoir) can be cycled or passed through the curvilinear microchannel until the desired level of concentration of blast cells is achieved and/or the desired volume of background fluid is directed to a reservoir other than the inlet reservoir and/or the desired number of particles larger than the blast cells are removed from the sample and/or the particles smaller than the blast cells are removed from the sample.

In inertial microfluidics, cells within a non-linear microchannel are subjected to two core forces; the net inertial lift force and the dean drag force [13]. A balance between these forces allows cells of different particle sizes to focus at respective positions along the microchannel. Focused streams of cells are separated by a strategically placed bifurcation point, allowing the separation of cells undergoing differential net forces.

Figure 2:
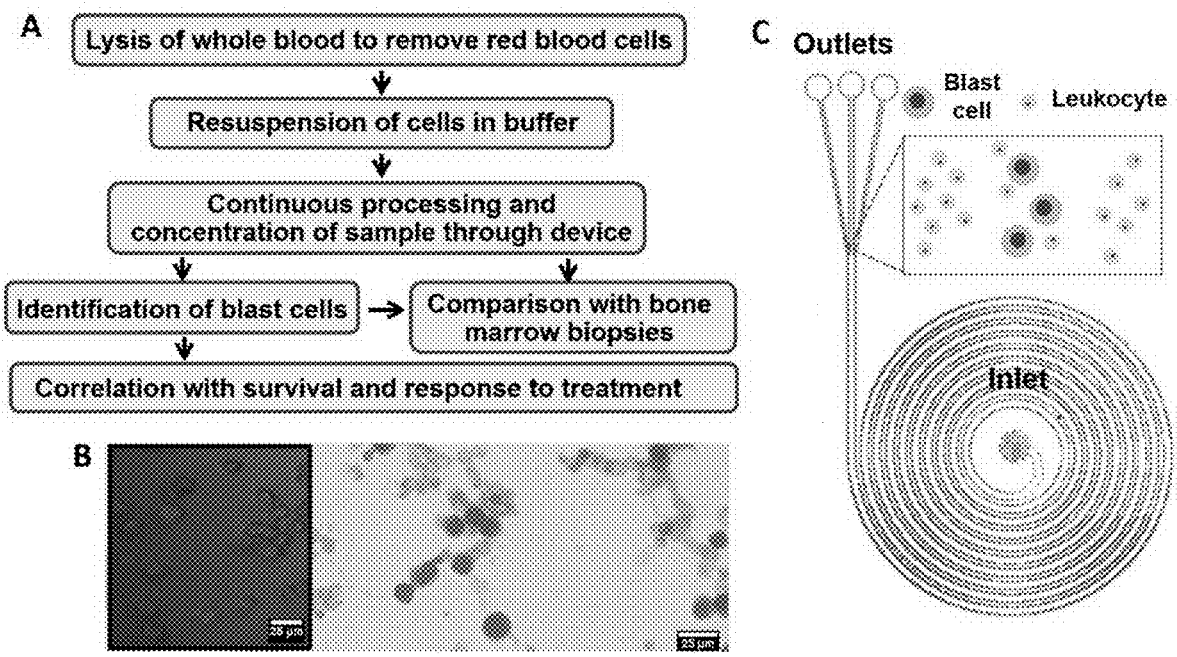
FIG. 2: A rapid procedure for enriching blast cells from blood for leukemia detection. (A) Workflow of procedures. (B) (Left) Merged image of the bright field and Hoechst for healthy blood spiked with Hoechst-stained blast cell lines. (Right) Histopathological staining of enriched blast cells after processing. (C) The layout of a closed-looped continuous flow system for rare cell enrichment and concentration. The sample is directed towards the three-outlet device with a peristaltic pump. Target cells from the middle outlet return to the sample source while non-target cells from the outer left and inner right outlets enter the waste outlet.
Figure 3:
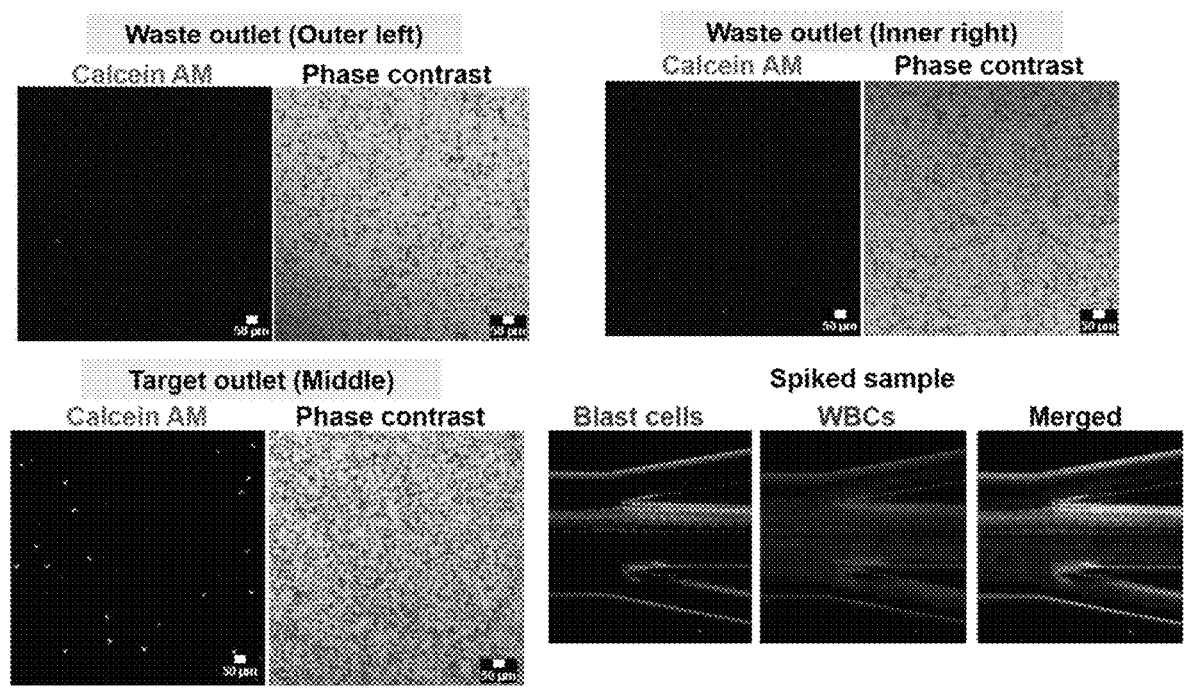
FIG. 3: Visualization of blast cell enrichment with the spiral microfluidic device. (A-C) Representative confocal images of sorted cell samples from target and waste outlets after processing. Blast target cells were stained with calcein AM (green). (D) Still frames captured with a high-speed camera to observe focused streams of target cells amongst the other blood cells.

The present invention includes a one-step continuous closed loop system to promote routine and affordable cancer management for leukemia patients (FIG. 1). Non-target cells (e.g. residual red blood cells and other white blood cells) encounter a differential net force as compared to stiffer blast cells of high nuclear to cytoplasmic ratio and enter the waste outlet (FIG. 2). The feedback loop to the sample source also allows continuous removal of smaller particles which cannot form a focused stream within the microchannel (FIG. 3).

FIG. 1 shows a modified three-outlet inertial-based device for the routine and affordable detection of blast cells from patients with leukemia. By feeding the target outlet back into the sample source, the concentration of particle/cell is maximized. Non-target cells (e.g. residual red blood cells and other white blood cells) encounter a differential net force as compared to stiffer blast cells of high nuclear to cytoplasmic ratio and enter the waste outlet (FIG. 2). The feedback loop to the sample source (the inlet reservoir) also allows continuous removal of smaller particles which cannot form a focused stream within the microchannel (FIG. 3). This is possible as the smaller particles which cannot form a focused stream within the microchannel are negatively collected at the waste. Hence these smaller particles are increasingly removed from the sample source after repeated cycles.

Figure 4:
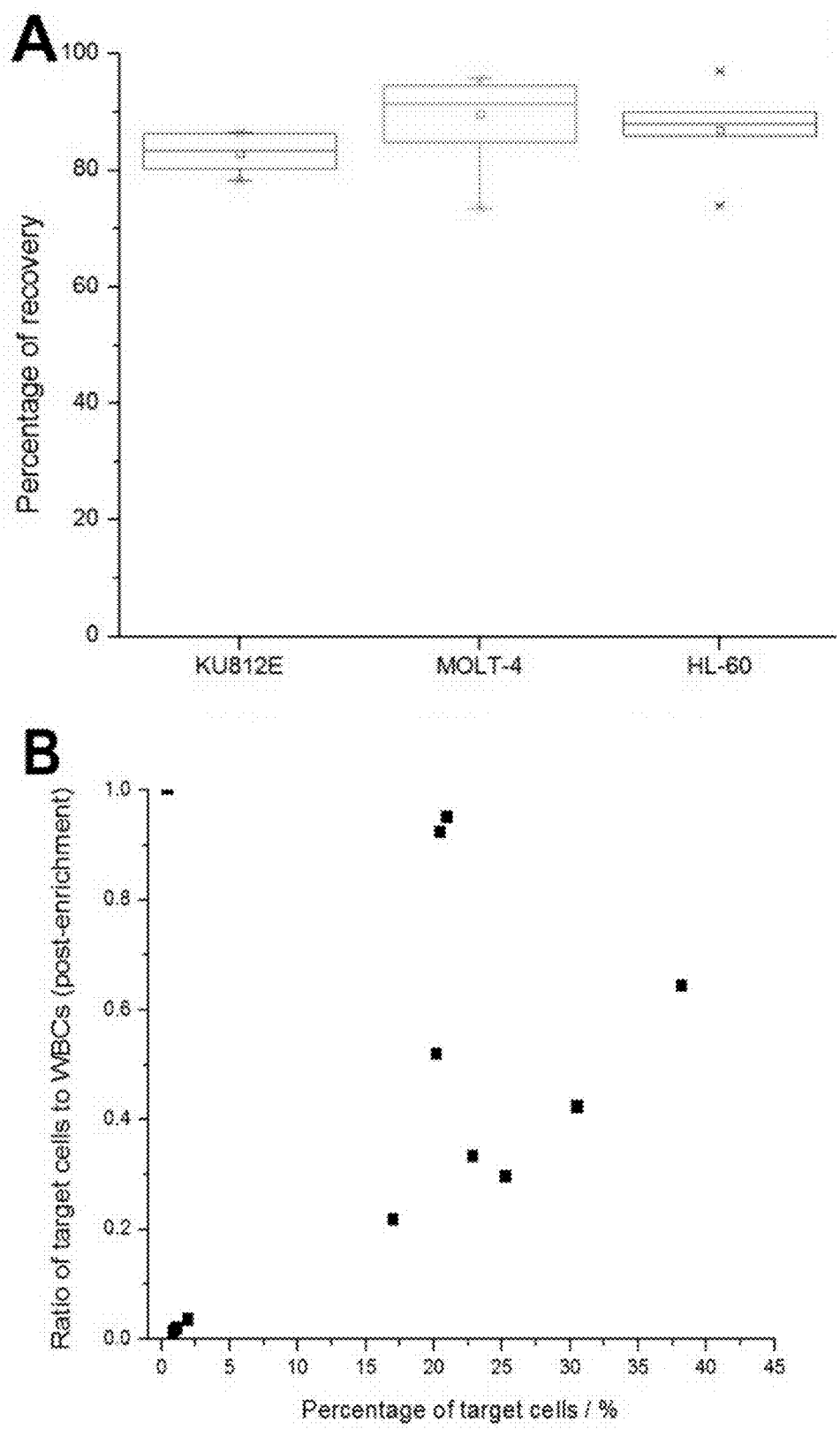
FIG. 4: Characterization of system robustness and blast cell enrichment efficiency. (A) Recovery percentages of different types of blast cell lines. (B) Scatter plot demonstrating variation in target cell recovery percentages across samples spiked with different target cell concentrations. (C) Scatter plot demonstrating variation in the purity of target cells post-enrichment across samples spiked with different target cell concentrations. (D) Bar chart demonstrates an increase of purity after recirculation of enriched sample.
Figure 4:
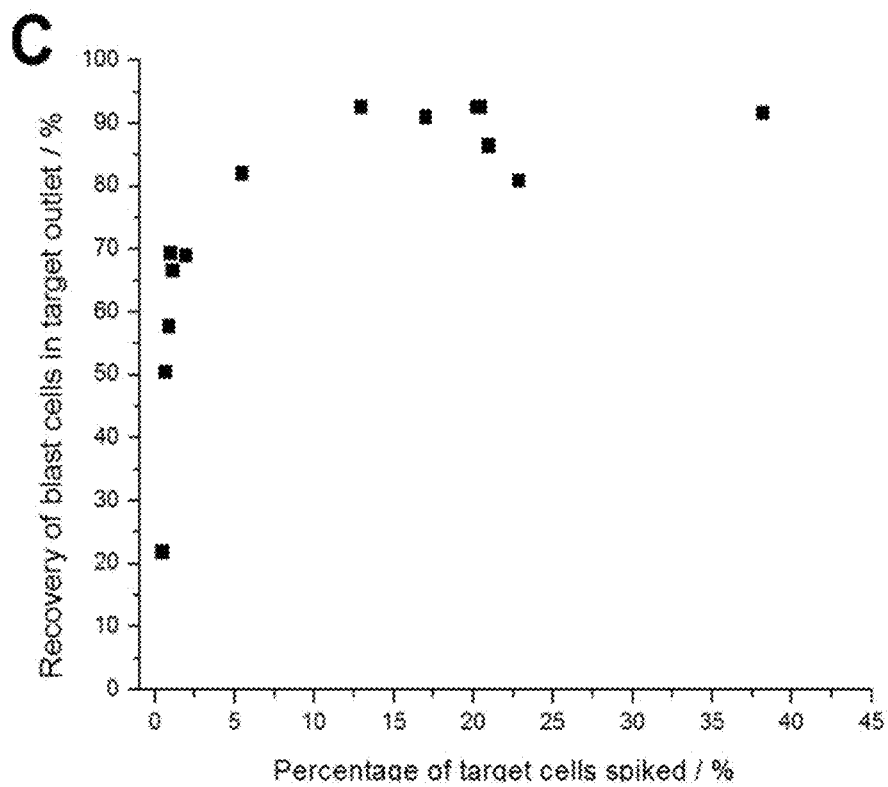
Figure 4:
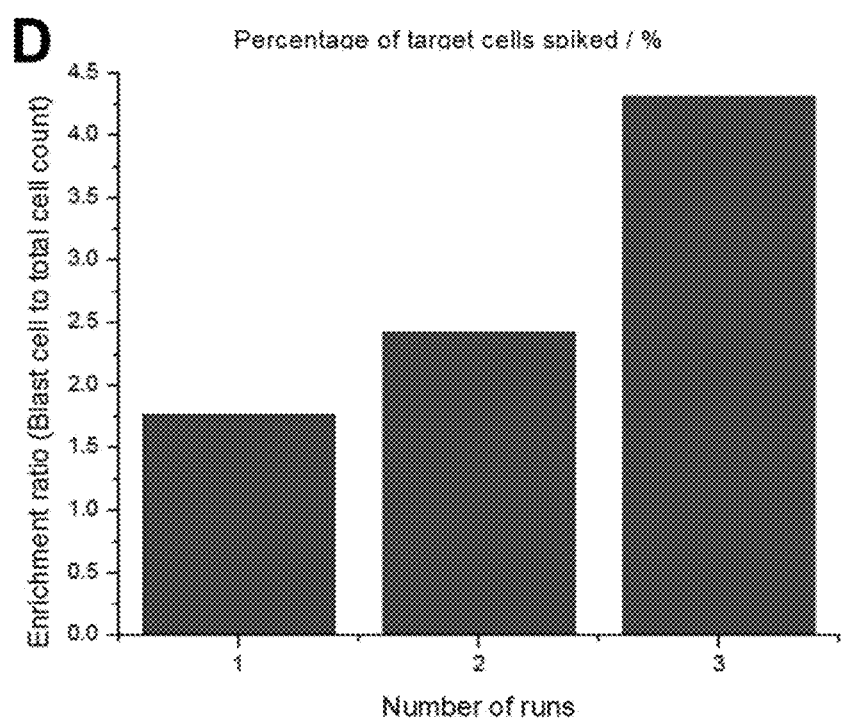

The application of the invention for detecting low counts of blast cells from blood was validated as shown in FIG. 4. Blood samples spiked with blast cells from the various leukemia cell lines were prepared for processing. Samples spiked with MOLT-4 representing clinical samples of blood from acute leukemia patients (with higher blast cell counts, >5%) demonstrate a consistent effectiveness of 89.8±4.4% recovery. Similar recovery efficiencies were observed for other leukemia cell lines (HL-60, 87.3±8.3% and KU812E, 86.5±4.6%). Although the concentration of target cells correlates with recovery efficiency, the system is able to retain an effective recovery rate of 68.5±1.4% for samples representing clinical samples of blood from patients with residual or chronic disease (with lower blast cell counts, <5%). This translates to the robust detection of disease in samples with at least 1 blast cell amongst 10,000 leukocytes (MRD $10^{-5}$). For samples with less than 1% of blast cells in blood, MRD is still around $10^{-4}$, demonstrating a vast detection range which makes it applicable to many patient types. The high recovery and concentration factor provide an opportunity to isolate blast cells from very small volume of blood, like a drop of blood from a fingertip.

Figure 5:
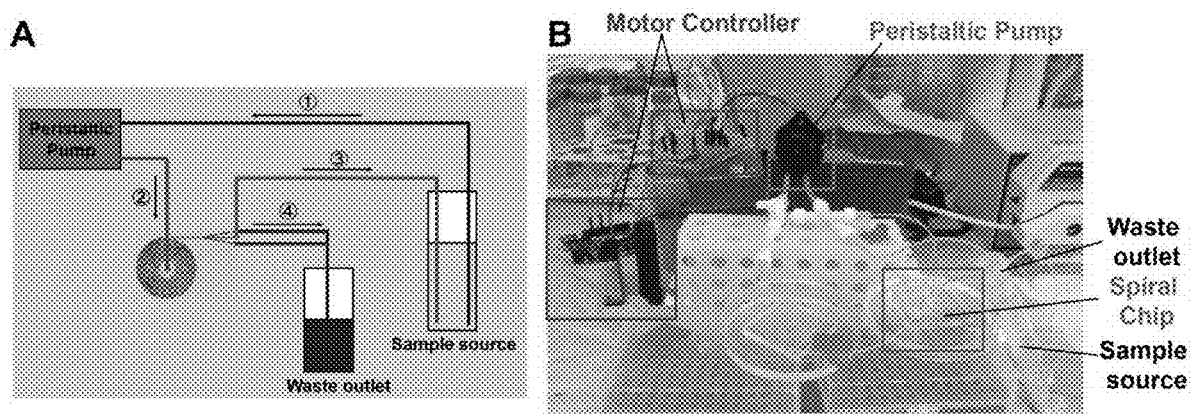
FIG. 5: Closed-looped microfluidics system for efficient recirculation. (A) Schematics of three-outlet microfluidics designed for blast cell enrichment. (B) A representative image of the actual set-up. The peristaltic pump is driven by batteries, which can be replaced with an AC unit for consistent force production.

The systems and methods allow continuous removal of non-target particles to generate concentrated samples, and can be highly effective for samples which cannot be purified (FIG. 5). Leukemia blast cells (about 13 to about 16 μm) share a similar cell size range with its background cells (about 8 to about 20 μm), which makes it difficult to purify the blast cells effectively in a single run. Recirculation of fluid within the inertial microfluidics cell sorting system allows the less stiff background cells (comprising platelets, residual red blood cells and leukocytes) to be increasingly removed from the sample source. This is especially true for small particles, such as red blood cells and platelets, which cannot be sorted into focused streams during flow within the microchannel. Hence the sample source containing the stiffer blast cells with higher nuclear to cytoplasmic ratio will be purified and concentrated. Enriched cancer samples can be utilized for downstream analysis, such as polymerase chain reactions, sequencing, immunostaining and fluorescence in situ hybridization.

The ability to detect leukemia with non-invasive and inexpensive techniques provides a powerful tool for clinicians to monitor residual disease and/or to enable early detection. Blood samples obtained with liquid biopsy is desirable as the samples can be routinely drawn for disease monitoring. The procedure is also relatively less invasive and does not risk increased mortality like surgical bone marrow biopsies.

Blast cells are present within a similar cell size range as compared to the background cells, preventing absolute purification with a single run. In this system, the purity ratio of enriched blast cells (determined by the ratio of target blast cells to other background cells) increases exponentially with the frequency of target cells in the sample (0.1 to 0.65 for samples with >5% blast cells; 0.005 to 0.34 for samples with <5% blast cells). The closed-loop system demonstrates an exponential increase for enrichment folds of the target blast cells with the number of runs through the system, relative to the concentration of pre-enriched samples. The invention is robust as evident by the linear enrichment ratio of target cell to background cell ratio across all initial concentrations of blast cells. In all cases, the device performs robustly to obtain an enrichment fold of 1.9±0.4. See FIG. 4.

To process clinical samples, whole blood from leukemia patients is withdrawn and processed within about 6 hrs to ensure optimal sample conditions. Blood samples are lysed briefly (see Materials and Methods) with RBC lysis buffer to remove red blood cells. We have previously evaluated the impact of RBC lysis on cell recovery [21] and did not observe any significant compromise to the viability or morphology of target cancer cells. Nucleated cell fraction containing white blood cells and blast cells are resuspended to 10 ml of saline buffer supplemented with surfactant. Poloxamer 188 is the surfactant introduced to prevent cells from sticking on the microchannels, promoting cell recovery and maximizing focusing of cells for sorting. The diluted sample is passed through the inertial-based device for several cycles until sample source is concentrated to about 500 ul. The concentrated sample can be further processed with specific dyes or antibodies to identify blast cells, and the enumerated blast cell counts can be used for correlation with bone marrow biopsy results. The variation of blast cells in peripheral blood samples and bone marrow biopsies can provide valuable information on patient prognosis and response.

A summary of the features and advantages of the systems and methods described herein is summarized in Table 1:

TABLE 1

| Feature | Benefit/Advantage |
| --- | --- |
| Continuous closed-looped flow system Interested parties: Biomedical engineers, Cancer cell biologists | Simultaneous concentration and purification of rare samples at the same time - 1) Unlike previous open-loop configuration where the volume of output could only be determined by bifurcation ratio or fluidic resistance ratio at the binary outlet, the closed-loop configuration can provide concentration factor as initial/final suspension volume ratio. This feature is not affected by micro-channel dimension or micro-structure, thus, provide flexibility for microfluidic architecture. 2) Applicable for sensitive downstream analysis such as gene sequencing panels which require concentrated and purified samples, i.e. enzymatic assay, PCR, cellular immune function assay etc. Isolation of small particles by negative selection, achieving high degrees of purification. Alternatively, small particles such as bacteria, protein or genetic material can be purified with the removal of larger cells. |
| System is mediated by simple, portable inertial-based microfluidic devices Interested parties: Oncologists | The simplicity of device set up allows potential multiplexing of the device, promoting concentration of large sample volumes, such as blood, urine or diluted biological samples. Due to the simplicity of the procedure, the protocols can be learned rapidly, with sufficient mastery to independently conduct experiments obtained under a week. Especially when compared with the lengthy training needed to conduct surgical or needle biopsies, enrichment via the present invention shows significant promise as low-cost, rapid, and straightforward method leukemia detection. |
| Detection and concentration of leukemia blast cells from blood Interested parties: Oncologists | 1) Blast cells can be detected from blood samples obtained via liquid biopsy (blood withdrawal) which is a relatively non-invasive technique, as compared to bone marrow biopsies, and does not risk increased mortality 2) High applicability in cases where the patient cannot handle routine (every few weeks) bone marrow screens. 3) Procedure can be carried out routinely, allowing the monitoring of disease |
| Continuous removal of background cells Interested parties: Biomedical engineers, Cancer cell biologists, | 1) Removal of background cells leads to high sensitivity of target cell detection (~MRD $10^{-6}$, which is more sensitive than current techniques), allowing the invention to be suitable for early stage diagnosis, detection of minimal residual disease or chronic stages of leukemia. 2) The system allows heightened purification of target cells, especially in samples which are not fully separated within a single run. 3) Heightened blast cell counts in the peripheral blood may reflect worsened prognosis. Therefore, the sensitivity of the invention will allow clinicians to revisit the current thresholds of blast cells in blood and promote early detection of leukemia for prompt intervention. |

Preferred microfluidics devices that can be used in the invention include those described in Lim et al., WO2011/109762A1; 9 Sep. 2011; Birch et al., WO 2013/181615; 5 Dec. 2013, Han et al., WO 2014/046621 A1; 27 Mar. 2014, Hou et al., WO 2014/152643 A1; 25 Sep. 2014; Voldman et al., WO 2015/156876 A2; 15 Oct. 2015; Warkiani et al., WO 2016/044537 A1; 24 Mar. 2016; Warkiani et al., WO 2016/044555 A1; 24 Mar. 2016; and Sarkar et al., WO 2016/077055 A1; 19 May 2016, which are each incorporated by reference in their entirety. In particular, devices which comprise a continuous closed-loop system, such as those described in U.S. Ser. No. 62/405,335 by Ryu et al., filed on Oct. 7, 2016, the contents of which are hereby incorporated by reference are preferred.

In microfluidic devices, particles flowing in curvilinear channels are influenced by both inertial migration and secondary Dean flows. The combination of Dean flow and inertial lift results in focusing and positioning of particles at distinct positions for concentration and separation applications.

It is preferred that the curved micro-channels have non-rectangular cross-sections, thereby resulting in the alteration of the shapes and positions of the Dean vortices which generate new focusing positions for particles. For example, as shown herein, a curved micro-channel with a deeper inner side (along the curvature center) and a shallow outer side generate two strong Dean vortex cores near the inner wall, trapping all particles irrespective of size within the vortex.

Preferred flow rates can be in a range of between about 0.5 mL/min and about 1 L/min, such as between 0.5 mL/min and about 10 mL/min. In some aspects, multiple channels can be combined into a single microfluidic device. In other aspects, multiple channels can be combined into a multiplexed microfluidic device.

A curved micro-channel with a shallow inner side and a deeper outer side skews the vortex centers near the outer wall at the outer side and can entrain particles and cells within the vortex. However, larger particles with dominant inertial force are focused near the inner channel walls, similar to rectangular cross-section channels. Thus, by designing appropriate channel parameters, small particles/cells are trapped in the vortex at the outside, while relatively large particles focus along the inner microchannel wall. The threshold diameter determining whether a particle/cell is trapped within the Dean vortex or focused towards the inner channel wall is dependent on the flow rate. This enables a device to achieve good separation resolution between mixtures having a wide range of particle sizes. In aspects two, three or more outlets can be used for collection. A trapezoidal cross-section facilitates higher particle/cell concentrations.

Several types of the curved channel (spiral, serpentine, arc) can be used. Spiral channels are preferred. Particles flowing in curved channels are influenced by both inertial force and Dean flow. The balance of these two effects can provide precise focusing and positioning of particles.

Fluid flowing through a channel with a laminar profile has a maximum velocity component near the centroid of the cross section of the channel, decreasing to zero near the wall surface. In a curved channel, the fluid experiences centrifugal acceleration directed radially outward. Since the magnitude of the acceleration is proportional to quadratic velocity, the centrifugal force in the centroid of the channel cross section is higher than at the channel walls. The non-uniform centrifugal force leads to the formation of two counter-rotating vortices known as Dean vortices in the top and bottom halves of the channel. Thus, particles flowing in a curvilinear channel experience a drag force due to the presence of these transverse Dean flows. Under Stokes' law, the drag force will be proportional to the Dean velocity at that point and proportional to the diameter of the particle. In the absence of other dominating forces, the Dean drag force will drive particles along the direction of flow within the vortex and finally entrain them within the core. In high aspect ratio rectangular cross section channels, this motion can be observed by observing particles moving back and forth along the channel width between the inner and outer walls with increasing downstream distance when visualized from the top or bottom.

Apart from the Dean drag force, larger cells with diameters comparable to the micro-channel dimensions also experience appreciable inertial lift forces resulting in their focusing and equilibration along the channel walls. In micro-channels with curvilinear geometry, the interplay between the inertial lift force and the Dean drag force reduces the equilibrium positions to just two near the inner channel wall at low flow rate, and move outward with an increase in flow rate, each within the top and bottom Dean vortex. The two equilibrium positions overlay each other along the micro-channel height and are located at the same distance from the micro-channel inner wall for a given cell size, i.e. viewed as a single position across the micro-channel width. Spiral microchannels with trapezoidal cross sections are preferred. These channels are different from the rectangular cross section, in that the maximum velocity is asymmetric along the channel cross-section resulting in the formation of stronger Dean vortex cores skewed towards the deeper channel side. These vortex cores have a high probability to entrain particles within them. As shown herein, in a spiral channel with a trapezoidal cross-section, the particle focusing behavior is different from that in a rectangular channel. In a trapezoidal channel, as shown in WO2014/046621, particles focus near the inner channel wall at low flow rate (similar to channels with a rectangular cross-section), while beyond a certain threshold flow rate, they switch to an equilibrium position located at the outer half.

Along the depth direction, according to experimental measurements, particles are focused between about 25.5-27.1% of the channel depth at flow rates of about 0.5-3.0 mL/min. This result indicates that the distance between the focused particle and the channel wall in a trapezoidal channel in the depth direction is larger than that in the rectangular channel.

If the inner wall of the channel is deeper, strong Dean vortices will appear at the inner side, i.e. particles will be trapped near the inner side, even at high flow rates. Curved channels with this cross section can be used to collect a larger size range of particles at the inner side of the outlet and filtered particle free liquid at the outer side of the outlet, finding numerous applications in water filtration, for example. On the other hand, if the outer wall of the channel is deeper, Dean vortices are skewed towards the outer side. At the inner side, the Dean flow field is much like that in a rectangular channel. At certain flow rates, the larger particle can focus along the inner wall influenced by both Dean flow and inertial lift, while the smaller particles tend to get trapped in the vortex center at the outer side.

Two typical regimes of focusing are based on particle size, the inertial dominant and Dean dominant regimes. For small particles (e.g., 5.78 µm particles), the large channel dimension prevented them from focusing and these particles got trapped in the Dean vortex even at low flow rate. The larger particles (e.g., about 9.77 µm particles) also could not focus at the inner wall and were trapped within the Dean vortices at flow rates greater than or equal to about 1 ml/min. For example, 15.5 µm particles focused at the inner wall at low flow rates, about 1.5 ml/min, but transitioned from the inertial dominant regime to Dean dominant regime at about 2 ml/min. For the same microchannel, the 26.25 µm particles transitioned from the inertial regime to Dean regime at flow rates about 3 ml/min. From these results, at a flow rate of about 1.5 ml/min, particles >about 15.5 µm can be separated from smaller ones by collecting from the inner and outer outlets separately. Similarly, at a flow rate of about 2.5 ml/min, about 26.25 µm particles can be separated from a mixture of about 26.25 µm and about 15.5 µm particles. In some aspects, a low flow rate can be in a range of between about 0.5 mL/min and about 2 mL/min. Utilizing these principals and the teachings herein, one of ordinary skill in the art can optimize the flow rate for separation of blast cells from components of a blood sample. Thus, a low flow rate can be a flow rate of about 0.5 mL/min, about 0.6 mL/min, about 0.7 mL/min, about 0.8 mL/min, about 0.9 mL/min, about 1.0 mL/min, about 1.1 mL/min, about 1.2 mL/min, about 1.3 mL/min, about 1.4 mL/min, about 1.5 mL/min, about 1.6 mL/min, about 1.7 mL/min, about 1.8 mL/min, about 1.9 mL/min, or about 2.0 mL/min.

Accordingly, in some aspects, the invention relates to a set of curved micro-channels with a non-rectangular cross-section that gives rise to unique Dean vortices for varying applications in a microfluidic field relating to particle focusing, separation, and mixing. In a particular aspect, the invention is directed to a method of separating blast cells comprising processing a sample in a microfluidic device and/or a method of detecting blast cells comprising processing a sample in microfluidic device, wherein the microfluidic device includes at least one inlet and a curvilinear microchannel having a trapezoidal cross section defined by a radially inner side, a radially outer side, a bottom side, and a top side, the cross section having a) the radially inner side and the radially outer side unequal in height, or b) the radially inner side equal in height to the radially outer side, and wherein the top side has at least two continuous straight sections, each unequal in width to the bottom side. The device further comprises at least two, preferably two or three outlets. In certain aspects, a spiral channel with a trapezoidal cross-section consisting of a shallow inner side and deeper outer wall is used.

In one aspect, the curvilinear microchannel can be a spiral microchannel as shown in FIG. 2. Alternatively, the curvilinear microchannel can be a serpentine microchannel. The curvilinear microchannel can have a radius of curvature in a range of between about 2.5 mm and about 25 mm. For example, the curvilinear microchannel can have a radius of curvature of about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm. The curvilinear microchannel can also have a length in a range of between about 4 cm and about 100 cm. For example, the curvilinear microchannel can have a length of about 5 cm, about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, or about 100 cm.

For a trapezoidal cross-section spiral microchannel, there are several factors that affect the focusing position and separation efficiency, such as the width of the microchannel, inner and outer depth of the microchannel cross-section, the radius of the spiral curvature, and the slant angle. The width can be in a range of between about 100 µm and about 2000 µm, such as a width of about 200 µm, about 300 µm, about 400 µm, about 500 µm, about 600 µm, about 700 µm, about 800 µm, about 900 µm, about 1000 µm, about 1100 µm, about 1200 µm, about 1300 µm, about 1400 µm, about 1500 µm, about 1600 µm, about 1700 µm, about 1800 µm, or about 1900 µm.

The outer depth can be in a range of between about 20 µm and about 200 µm, such as an outer depth of about 40 µm, about 60 µm, about 80 µm, about 100 µm, about 120 µm, about 140 µm, about 160 µm, or about 180 µm. The inner depth can be in a range of between about 20 µm and about 200 µm, such as an inner depth of about 40 µm, about 60 µm, about 80 µm, about 100 µm, about 120 µm, about 140 µm, about 160 µm, or about 180 µm. The radius of curvature can be in a range of between about 2.5 mm and about 25 mm, such as a radius of about 5 mm, about 7.5 mm, about 10 mm, about 12.5 mm, about 15 mm, about 17.5 mm, about 20 mm, or about 22.5 mm.

The slant angle is the angle between the top of the channel and the bottom of the channel. The slant angle can be in a range of between about 2 degrees and about 60 degrees. Thus, the slant angle can be about 2 degrees, about 4 degrees, about 6 degrees, about 8 degrees, about 10 degrees, about 12 degrees, about 14 degrees, about 16 degrees, about 18 degrees, about 20 degrees, about 22 degrees, about 24 degrees, about 26 degrees, about 28 degrees, about 30 degrees, about 32 degrees, about 34 degrees, about 36 degrees, about 38 degrees, about 40 degrees, about 42 degrees, about 42 degrees, about 46 degrees, about 48 degrees, about 50 degrees, about 52 degrees, about 54 degrees, about 56 degrees, about 58 degrees, or about 60 degrees. The slant angle of the channel affects the focusing behavior in two ways: (i) the threshold flow rate required to trap particles in the Dean vortex as a function of particle size and (ii) the location of the Dean vortex core. A large slant angle (i.e., in a range of between about 10 degrees and about 60 degrees) will lead to strong Dean at the outer side and increase the particle trapping capability. A large slant angle can also decrease the threshold flow rate required to trap particles of a given size within the Dean vortex.

The cross section of the channel can be characterized by a height of the radially inner side that is larger than a height of the radially outer side, or vice versa. In yet other aspects, the profile of the cross section can be stepped, curved, convex, or concave.

In other aspects, the radially inner side and the radially outer side of the trapezoidal cross section can have a height in a range of between about 20 microns (µm) and about 200 µm. Thus, the height of the radially inner side 210 can be about 20 µm, about 40 µm, about 60 µm, about 80 µm, about 100 µm, about 120 µm, about 140 µm, about 160 µm, about 180 µm, or about 200 µm, and the height of the radially outer side 220 can be about 20 µm, about 40 µm, about 60 µm, about 80 µm, about 100 µm, about 120 µm, about 140 µm, about 160 µm, about 180 µm, or about 200 µm. In some aspects, the height of the radially inner side 210 can be about 70 µm, or about 80 µm, or about 90 µm, and the height of the radially outer side 220 can be about 100 µm, or about 120 µm, or about 130 µm, or about 140 µm.

In certain aspects, the top side and the bottom side of the trapezoidal cross section can have a width in a range of between about 100 µm and about 2000 µm, such as a width of about 200 µm, about 300 µm, about 400 µm, about 500 µm, about 600 µm, about 700 µm, about 800 µm, about 900 µm, about 1000 µm, about 1100 µm, about 1200 µm, about 1300 µm, about 1400 µm, about 1500 µm, about 1600 µm, about 1700 µm, about 1800 µm, or a width of about 1900 µm.

Spiral microchannels can comprise one or more loops. In certain aspects, the multi-loop microchannel can be a 2 loop microchannel, a 3 loop microchannel, a 4 loop microchannel a 5 loop microchannel, a 6 loop microchannel, a 7 loop microchannel, an 8 loop microchannel, a 9 loop microchannel, a 10 loop microchannel, etc. In a particular aspect, the multi-loop microchannel can be an 8-loop microchannel. In one specific aspect of an 8 loop microchannel, the device can be an 8-loop spiral microchannel with one inlet and two outlets with radius of curvature decreasing from about 24 mm at the inlet to about 8 mm at the two outlets for efficient cell migration and focusing. The width of the channel cross-section can be about 600 µm and the inner/outer heights can be about 80 µm and about 130 µm, respectively, for the trapezoid cross-section.

As will also be appreciated by those of skill in the art, the microfluidic device can further comprise other components upstream, downstream, or within a device. For example, one or more microfluidic devices can further comprise one or more collection devices (e.g., a reservoir), flow devices (e.g., a syringe, pump, pressure gauge, temperature gauge), analysis devices (e.g., a 96-well microtiter plate, a microscope), filtration devices (e.g., a membrane), e.g., for upstream or downstream analysis (e.g., immunostaining, polymerase chain reaction (PCR) such as reverse PCR, quantitative PCR), fluorescence (e.g., fluorescence in situ hybridization (FISH)), sequencing, and the like. An imaging system may be connected to the device, to capture images from the device, and/or may receive light from the device, in order to permit real time visualization of the isolation process and/or to permit real time enumeration of isolated cells. In one example, the imaging system may view and/or digitize the image obtained through a microscope when the device is mounted on a microscope slide. For instance, the imaging system may include a digitizer and/or camera coupled to the microscope and to a viewing monitor and computer processor.

Blast cells can be readily concentrated and isolated by the device from a biological sample. A blood sample, for example, can be whole blood or the blood can be introduced unadulterated or adulterated (e.g., lysed, diluted). Methods of lysing blood are known in the art. In some aspects, the volume to volume concentration of the particles as compared to other cells can be less than about 5%. Thus, the volume to volume concentration can be about 4%, about 3%, or about 2%. In some aspects, dilution of the blood sample can be to a hematocrit in a range of between about 0.5% and about 2%. Thus, the hematocrit of a diluted blood sample can be about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2%.

In the methods described herein, fluid can be introduced and recirculated into the microfluidic device in a variety of ways. In one aspect, fluid can be introduced into the microfluidic device using a syringe pump. In other aspects, fluid can be introduced into the microfluidic device using a piston pump, a gear pump, a peristaltic pump, a piezoelectric micropump, or using a controllable pressure regulator. The flow rate of fluid through the microfluidic device will vary depending on the use. In some aspects, the flow rate can be in a range of between about 0.5 mL/min and about 10 mL/min, such as a flow rate of about 1 mL/min, about 2 mL/min, about 3 mL/min, about 4 mL/min, about 5 mL/min, about 6 mL/min, about 7 mL/min, about 8 mL/min, or about 9 mL/min.

The methods described herein can further comprise collecting and isolating blast cells. In certain aspects, the method can further comprise downstream analysis such as immunostaining, qRT-PCR, FISH and sequencing.

In the methods described herein, unless otherwise specified, the capture efficiency of blast cells can be in a range of between about 60% and about 100%, such as about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, and about 99%; or at least about 62%, at least about 64%, at least about 66%, at least about 68%, at least about 70%, at least about 72%, at least about 74%, at least about 76%, at least about 78%, at least about 80%, at least about 82%, at least about 84%, at least about 86%, at least about 88%, at least about 90%, at least about 92%, at least about 94%, at least about 96%, at least about 98%, and at least about 99%. In a particular aspect, the capture efficiency can be an average recovery of about 80%, or about 85%, or about 87%. In additional aspects, the capture efficiency can be an average recovery of at least bout 80%, or at least about 85%, or at least about 87%.

Microfluidic channels can be cast from a polymethylmethacrylate (PMMA) mold made by a precision milling process (Whits Technologies, Singapore). The design consists of one or two inlets, two or three outlet spiral channel with multiple loops and a curvature radius of about 10 mm. The patterns can be cast with Sylgard 184 Silicone Elastomer (PDMS) prepolymer mixed in a 10:1 ratio with the curing agent and cured under 80 C for 2 hours. After curing, the PDMS mold with patterns can be peeled and plasma bonded to another 3 mm thick PDMS layer. Input and output ports can be punched prior to bonding. For the observation of particle position from the side, the device can be cut along the output section of the channel with about 2 mm distance and then a second cast can be made by keeping the device vertical to a flat bottle container. Tubings can be connected to the ports before the second cast to prevent PDMS mixer flow into the channel.

In certain additional aspects, the invention includes a microfluidic system for detecting blast cells in a blood sample comprising:
i. At least one inlet reservoir;
ii. At least one output reservoir;
iii. A first curvilinear microchannel comprising a first inlet in fluid communication with an inlet reservoir, a first outlet in fluid connection with the inlet reservoir, and a second outlet in fluid communication with an output reservoir, and a third outlet in fluid communication with the output reservoir; wherein said curvilinear microchannel is configured to separate blast cells from a blood sample;

wherein the microfluidic system is configured to provide a closed-loop recirculation of the sample in the inlet reservoir through the first curvilinear microchannel. In certain embodiments, the second outlet is located on the radially inner side of the microchannel, wherein the third outlet is located on the radially outer side or the microchannel, and wherein the first outlet is located on the microchannel between the second and third outlets.

In yet further aspect, the invention is directed to a device comprising the microfluidic system. In further embodiments, the invention includes a portable device comprising the micro-fluidic systems described herein. In certain aspects, the device comprises a micro-fluidic system as described herein one or more components upstream, downstream, and/or within a device. For example, the device can further comprise one or more collection devices (e.g., a reservoir), flow devices (e.g., a syringe, pump, pressure gauge, temperature gauge), analysis devices (e.g., a 96-well microtiter plate, a microscope), filtration devices (e.g., a membrane), e.g., for upstream or downstream analysis (e.g., immunostaining, polymerase chain reaction (PCR) such as reverse PCR, quantitative PCR), fluorescence (e.g., fluorescence in situ hybridization (FISH)), sequencing, and the like. In certain aspects, the device further comprises a pump, for example, one or more peristaltic pumps and/or piezoelectric pumps. An imaging system may be connected to the device, to capture images from the device, and/or may receive light from the device, in order to permit real time visualization of the isolation process and/or to permit real time enumeration of isolated cells. In one example, the imaging system may view and/or digitize the image obtained through a microscope when the device is mounted on a microscope slide. For instance, the imaging system may include a digitizer and/or camera coupled to the microscope and to a viewing monitor and computer processor.

The invention is illustrated by the following examples which are not meant to be limiting in any way.

EXEMPLIFICATION

Materials and Methods
Cell Culture

Human leukemia blast cell lines (MOLT-4, HL-60 and KU812E) were cultured in an incubator (ThermoFisher Scientific, Heracell 150i) at 37° C. and 5% CO2 in supplemented RPMI media (Life Technologies, 11875-119). Media was supplemented with 10% fetal bovine serum (FBS) and 1% penstrep (penicillin G and streptomycin) (all from Invitrogen, Carlsbad, Calif.). The cell media was changed every 2-3 days, and cells were harvested when their confluency reached 80%.

Cell Harvesting

Media was aspirated from the cell culture flask, and 1 mL of PBS was added (Vivantis Inc, Cat # PB0344-1L). The flask was gently shaken to remove debris and dead cells, and the PBS was aspirated. 1 mL of trypsin (Gibco, Ref #25300-054) was added to the cell flask, which was placed into the incubator at 37° C. and 5% CO2 for 5 minutes. Afterwards, 1 mL of fresh media was added to terminate the reaction. The contents of the cell culture flask were transferred to a Falcon tube (Corning, Ref #352096) and centrifuged for 3 minutes at 1200 rpm (Beckman Coulter, Allegra X-15R). The supernatant was aspirated, and cells were resuspended in 1 mL PBS.

Labeling with Cytoplasmic Dye

200 μL of cell suspension and 50 μL of PBS were mixed in an Eppendorf tube. 1 μL of Celltracker Green (Life Technologies, Ref # C2925, Eugene) was pipetted into the tube, which was placed into an ice box for 10 minutes. 1 mL of PBS was added the Eppendorf tube, which was centrifuged for 3 minutes at 1200 rpm. The supernatant was aspirated and the pellet resuspended in 1 mL PBS. The centrifugation and resuspension steps were repeated.

Lysis of Whole Blood for Processing

RBC lysis was done to obtain nucleated cells for processing. Blood was mixed with RBC lysis buffer (1:3 ratio; Life Technologies, Carlsbad, Calif.) under gentle agitation for a maximum of 3 mins, and centrifuged at 1000 g for 5 mins to concentrate the intact nucleated cells. The supernatant containing lysed RBC debris and plasma were decanted, and the resultant cell pellet was immediately washed once with PBS.

Preparation of Spiked Blood Samples

The concentration of stained cells was calculated using a hemocytometer (NanoEnTek, Neubauer Improved DHC-N01), and respective counts of blast cells were added to a corresponding volume of blood from a healthy donor. To accurately determine the spiked cell counts, three sets of 100 ul cell stock were imaged in wells of a 96 well plate. The average counts were obtained to arrive at the initial spiked cell count. The final spiked cell suspension was diluted with PBS to a total volume of 10 mL and treated with 300 μL 0.2% of Poloxamer 188 solution (Sigma-Aldrich, Ref # P5556) prior to processing within the system.

System Processing

Figure 6:
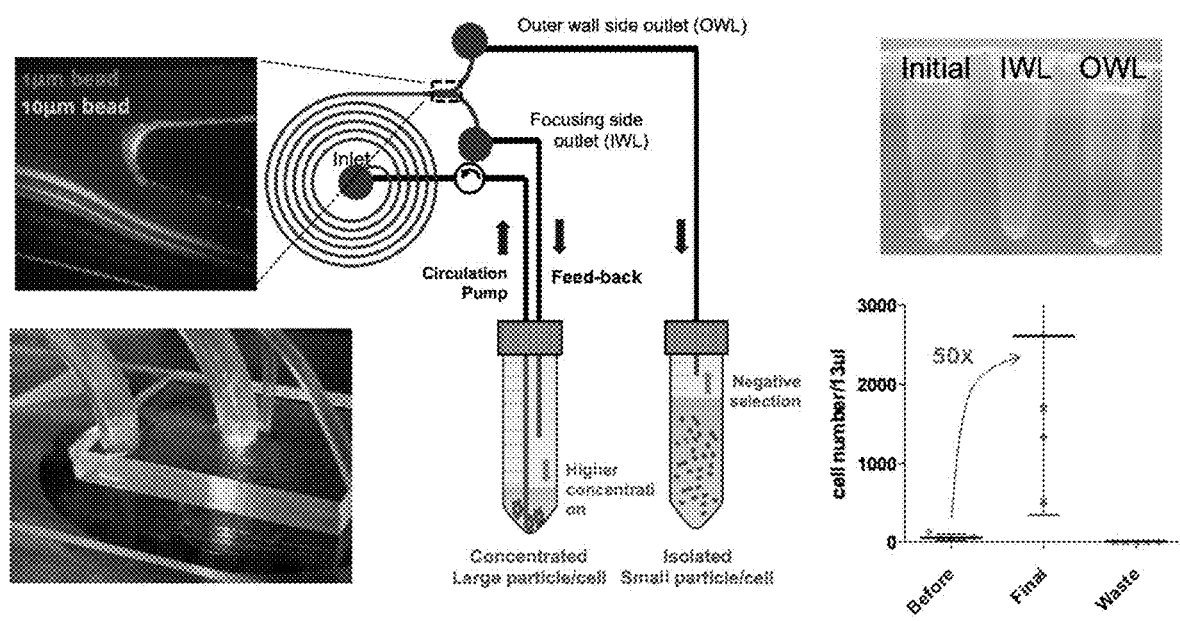
FIG. 6: An illustration of a closed-loop spiral microfluidics device suitable for use in the invention. The closed-loop spiral microfluidics device includes two outlets. The focusing side (IWL) outlet directs fluid to the inlet reservoir where the fluid can be recirculated into the spiral microchannel. The outer wall side outlet (OWL) directs fluid to the output reservoir.
Figure 7:
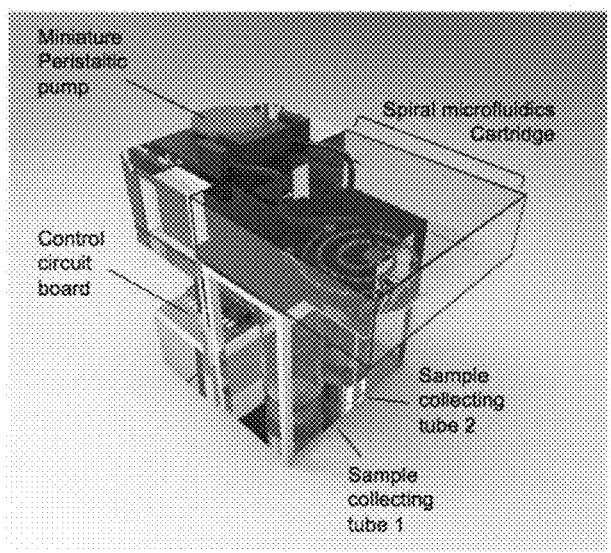
FIG. 7: A proposed closed-loop spiral microfluidics separation system including a miniature peristaltic pump, conical tube, control circuits and microfluidics. This feature provides the possibility to minimize the cost as well as size to offer cell-based diagnostics for the country without proper biological equipment where this type of diagnostics is most needed.

A peristaltic pump (SG Biotic, Singapore) was used to flow the cell solution through a three-outlet spiral microfluidic device at 1.5 mL/min, collecting solutions from the target middle and waste outlets (extreme left and right) separately. Prior to the first enrichment round, the chip was primed by flowing PBS for 60 seconds at 1.5 mL/min. The solution from the target middle channel was recirculated into the device until the final volume of the inner outlet solution was approximately 500 μL. Enriched samples were placed in the 96-well plate for imaging and enumeration. If the force exerted by the peristaltic pump is too high, the sample can be split to reduce the final flow rate before entering the device. Images of a closed-loop spiral microfluidics system suitable for use in the invention are presented in FIG. 6. Alternatively, a portable and low cost closed-loop spiral microfluidics separation system for cell-based diagnostics in countries without proper biological equipment can be utilized, as presented in FIG. 7.

Fluorescence Microscopy and Data Analysis

Samples in the 96-well plate were imaged with an inverted confocal microscope (Olympus Fluoview FV1000, USA), and cell counting was automated with a custom Image script.

Histological Staining of Enriched Blast Cells

Histopathological morphology of the cultured cells was observed via standard Wright-Giemsa staining procedures at the Department of Haematology, National University of Singapore. Staining was done on frosted slides (Thermo Fisher Scientific) with cell spots fixed in methanol.

The relevant teachings of all patents, published applications and references cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims. It should also be understood that the preferred embodiments described herein are not mutually exclusive and that features from the various preferred embodiments may be combined in whole or in part in accordance with the invention.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference. The relevant teachings of all patents, published applications and references cited herein are incorporated by reference in their entirety.

REFERENCES

1. Gansler, T., et al., *Sixty years of CA: a cancer journal for clinicians*. CA Cancer J Clin, 2010. 60(6): p. 345-50.
2. Mantovani, A., *Cancer: Inflaming metastasis*. Nature, 2009. 457(7225): p. 36-7.
3. Khoo, B. L., et al., *Genesis of Circulating Tumor Cells Through Epithelial-Mesenchymal Transition as a Mechanism for Distant Dissemination*, in *Circulating Tumor Cells*. 2016, Springer.
4. Basik, M., et al., *Biopsies: Next-generation biospecimens for tailoring therapy*. Nat. Rev. Clin. Oncol., 2013. 10: p. 437-450.
5. de Bono, J. S., et al., *Circulating tumor cells predict survival benefit from treatment in metastatic castration-resistant prostate cancer*. Clin Cancer Res, 2008. 14(19): p. 6302-9.
6. Khoo, B. L., et al., *Short-term expansion of breast circulating cancer cells predicts response to anti-cancer therapy*. Oncotarget, 2015 (accepted).
7. Nole, F., et al., *Variation of circulating tumor cell levels during treatment of metastatic breast cancer: prognostic and therapeutic implications*. Ann Oncol, 2008. 19(5): p. 891-7.
8. Frisch, B. and R. Bartl, *Bone marrow histology in myelodysplastic syndromes*. Scand J Haematol Suppl, 1986. 45: p. 21-37.
9. Whitesides, G. M., *The origins and the future of microfluidics*. Nature, 2006. 442(7101): p. 368-373.
10. Bastos-Oreiro, M., et al., *Prognostic impact of minimal residual disease analysis by flow cytometry in patients with acute myeloid leukemia before and after allogeneic hemopoietic stem cell transplantation*. Eur J Haematol, 2014. 93(3): p. 239-46.

11. Martinez-Lopez, J., et al., *Prognostic value of deep sequencing method for minimal residual disease detection in multiple myeloma*. Blood, 2014. 123(20): p. 3073-9.
12. Strati, P., et al., *Eradication of bone marrow minimal residual disease may prompt early treatment discontinuation in CLL*. Blood, 2014. 123(24): p. 3727-32.
13. Warkiani, M. E., et al., *Ultra-fast, label-free isolation of circulating tumor cells from blood using spiral microfluidics*. Nat Protoc, 2016. 11(1): p. 134-48.
14. Warkiani, M. E., et al., *Slanted spiral microfluidics for the ultra-fast, label-free isolation of circulating tumor cells*. Lab on a Chip, 2014. 14(1): p. 128-137.
15. Warkiani, M. E., et al., *Malaria detection using inertial microfluidics*. Lab Chip, 2015. 15(4): p. 1101-9.
16. Nima, Z. A., et al., *Circulating tumor cell identification by functionalized silver-gold nanorods with multicolor, super-enhanced SERS and photothermal resonances*. Sci Rep, 2014. 4: p. 4752.
17. Nagrath, S., et al., *Isolation of rare circulating tumour cells in cancer patients by microchip technology*. Nature, 2007. 450(7173): p. 1235-9.
18. Jing, T., et al., *Jetting microfluidics with size-sorting capability for single-cell protease detection*. Biosens Bioelectron, 2015. 66: p. 19-23.
19. Di Carlo, D., *Inertial microfluidics*. Lab Chip, 2009. 9(21): p. 3038-46.
20. Kuntaegowdanahalli, S. S., et al., *Inertial microfluidics for continuous particle separation in spiral microchannels*. Lab Chip, 2009. 9(20): p. 2973-80.
21. Warkiani, M. E., et al., *An ultra-high-throughput spiral microfluidic biochip for the enrichment of circulating tumor cells*. Analyst, 2014. 139(13): p. 3245-55.

What is claimed is:

1. A method of detecting blast cells in a blood sample comprising the steps of:
   a. introducing a blood sample into an inlet reservoir of a microfluidic system comprising:
      i. At least one inlet reservoir;
      ii. At least one output reservoir;
      iii. A first curvilinear microchannel comprising a first inlet in fluid communication with an inlet reservoir, a first outlet in fluid connection with the inlet reservoir, and a second outlet in fluid communication with an output reservoir; wherein said curvilinear microchannel is configured to separate particles from a fluid comprising a mixture of particles and wherein the microfluidic system is configured to provide a closed-loop recirculation of the fluid through the first curvilinear microchannel;
   b. directing the blood sample from the inlet reservoir into the first inlet of the first curvilinear microchannel, bifurcating the blood sample into a first stream containing blast cells and at least one additional stream, wherein the at least one additional stream contains waste;
   c. directing the first stream to the inlet reservoir and the second stream to the output reservoir, wherein the first stream comprises blast cells; and
   d. detecting blast cells in the first stream.

2. The method of claim 1, wherein the curvilinear microchannel is a spiral microchannel or a serpentine microchannel.

3. The method of claim 2, wherein the microchannel is a spiral microchannel comprising at least 4 loops.

4. The method of claim 1 wherein the curvilinear microchannel has a trapezoidal cross section defined by a radially inner side, a radially outer side, a bottom side, and a top side, the cross section having a) the radially inner side and the radially outer side unequal in height, or b) the radially inner side equal in height to the radially outer side, and wherein the top side has at least two continuous straight sections, each unequal in width to the bottom side.

5. The method of claim 4 wherein the curvilinear microchannel cross section has (a) the height of the radially inner side larger than the height of the radially outer side, or (b) the height of the radially inner side is smaller than the height of the radially outer side, or (c) the top side includes at least one step forming a stepped profile, or (d) the top side includes at least one shallow region in between the radially inner side and the radially outer side.

6. The method of claim 4, wherein the microchannel has a right trapezoidal cross section.

7. The method of claim 4, wherein the radially inner side of at least one microchannel cross section has a height in a range of between about 20 microns and about 200 microns.

8. The method of claim 4, wherein the radially outer side of at least one microchannel cross section has a height in a range of between about 20 microns and about 200 microns.

9. The method of claim 4, wherein the bottom side of at least one microchannel cross section has a width in a range of between about 100 microns and about 2000 microns.

10. The method of claim 4, wherein the top side of at least one microchannel cross section has a width in a range of between about 100 microns and about 2000 microns.

11. The method of claim 4, wherein at least one curvilinear microchannel has a radius of curvature in a range of between about 2.5 mm and about 25 mm.

12. The method of claim 4, wherein at least one curvilinear microchannel has a length in a range of between about 4 cm and about 100 cm.

13. The method of claim 1, wherein the first inlet of the first curvilinear microchannel is the only inlet of the first curvilinear microchannel.

14. The method of claim 13, wherein the first inlet is on the interior of a spiral microchannel.

15. The method of claim 14, wherein the outlets are on the circumference of a spiral microchannel.

16. The method of claim 1, wherein the first outlet is located on the radially outer side of the microchannel.

17. The method of claim 16, wherein the system comprises at least one additional outlet and wherein the first outlet is located between the second outlet and the at least one additional outlet.

18. The method of claim 17, wherein the at least one additional outlet is in fluid communication with a second output reservoir or is in fluid communication with the same output reservoir as the second outlet.

19. The method of claim 1, wherein the first curvilinear microchannel comprises a third outlet.

20. The method of claim 19, wherein the third outlet is in fluid communication with a second output reservoir or is in fluid communication with the same output reservoir as the second outlet.

21. The method of claim 19, wherein at least one of the second and third outlets are located on the radially inner side of the microchannel.

22. The method of claim 19, wherein at least one of the second and third outlets are located on the radially outer side of the microchannel.

23. The method of claim 19, wherein the second outlet is located on the radially inner side of the microchannel, wherein the third outlet is located on the radially outer side or the microchannel, and wherein the first outlet is located on the microchannel between the second and third outlets.

24. The method of claim 1, further comprising a pump configured to pump fluid from the first reservoir to the inlet of the first curvilinear microchannel.

25. The method of claim 1, further comprising the step of lysing red blood cells in the blood sample prior to introducing the sample into the device.

26. The method of claim 1, wherein the step of detecting blast cells comprises immunostaining.

27. A method for separating blast cells from a blood sample comprising the steps of:
   a. introducing a blood sample into an inlet reservoir of a microfluidic system comprising:
      i. At least one inlet reservoir;
      ii. At least one output reservoir;
      iii. A first curvilinear microchannel comprising a first inlet in fluid communication with an inlet reservoir, a first outlet in fluid connection with the inlet reservoir, and a second outlet in fluid communication with an output reservoir; wherein said curvilinear microchannel is configured to separate particles from a fluid comprising a mixture of particles and wherein the microfluidic system is configured to provide a closed-loop recirculation of the fluid through the first curvilinear microchannel;
   b. directing the blood sample from the inlet reservoir into the first inlet of the first curvilinear microchannel, bifurcating the blood sample into a first stream containing blast cells and at least one additional stream, wherein the at least one additional stream contains waste;
   c. directing the first stream to the inlet reservoir and the second stream to the output reservoir, wherein the first stream comprises blast cells; and
   d. collecting the first stream from the inlet reservoir.

* * * * *